(12) United States Patent
Kumar et al.

(10) Patent No.: US 10,245,368 B2
(45) Date of Patent: Apr. 2, 2019

(54) INTEGRATED HYBRID BIO-ARTIFICIAL LIVER BIOREACTOR DESIGN AND METHOD THEREOF

(71) Applicant: Indian Institute of Technology, Kanpur, Kanpur, Uttar Pradesh (IN)

(72) Inventors: Ashok Kumar, Uttar Pradesh (IN); Apeksha Damania, Uttar Pradesh (IN)

(73) Assignee: INDIAN INSTITUTE OF TECHNOLOGY, KANPUR, Kanpur (IN)

(\*) Notice: Subject to any disclaimer, the term of this patent is extended or adjusted under 35 U.S.C. 154(b) by 254 days.

(21) Appl. No.: 15/224,055

(22) Filed: Jul. 29, 2016

(65) Prior Publication Data
US 2017/0252500 A1    Sep. 7, 2017

(30) Foreign Application Priority Data

Mar. 7, 2016   (IN) .............. 201611007880

(51) Int. Cl.
| | |
|---|---|
| *A61M 1/16* | (2006.01) |
| *A61M 1/34* | (2006.01) |
| *A01N 1/02* | (2006.01) |
| *C12M 1/00* | (2006.01) |
| *A61F 2/02* | (2006.01) |

(52) U.S. Cl.
CPC ......... *A61M 1/3489* (2014.02); *A01N 1/0221* (2013.01); *A01N 1/0236* (2013.01); *A01N 1/0247* (2013.01); *A61F 2/022* (2013.01); *A61M 1/16* (2013.01); *C12M 23/34* (2013.01); *C12M 29/04* (2013.01); *C12M 29/10* (2013.01)

(58) Field of Classification Search
CPC .............. A61M 1/3489; A61M 1/3472; A61M 1/3479; A61M 1/16; A61M 1/3486; A61M 2205/103; A01N 1/0247; A01N 1/0221; A01N 1/0236; C12M 23/34; C12M 23/02; C12M 25/16; C12M 29/10; C12M 29/04; A61F 2/022
USPC .............................. 435/289.1, 297.2, 297.4
See application file for complete search history.

(56) References Cited

U.S. PATENT DOCUMENTS

| | | | | |
|---|---|---|---|---|
| 5,605,835 | A * | 2/1997 | Hu ................. | A61F 2/022 435/297.2 |
| 5,919,369 | A * | 7/1999 | Ash ................. | A61M 1/3472 210/195.1 |
| 7,160,719 | B2 | 1/2007 | Nyberg et al. | |
| 2013/0217127 | A1* | 8/2013 | Kumar ........... | C08F 220/34 435/397 |

FOREIGN PATENT DOCUMENTS

| | | |
|---|---|---|
| CN | 2638736 Y | 9/2004 |
| WO | 1992007615 | 5/1992 |
| WO | 2016015371 A1 | 2/2016 |

\* cited by examiner

*Primary Examiner* — Michael L Hobbs
*Assistant Examiner* — Liban M Hassan
(74) *Attorney, Agent, or Firm* — King & Schickli, PLLC (57) ABSTRACT

The present invention relates to the field of bio-artificial liver technology. Particularly, the invention provides an integrated hybrid bio-artificial liver support system that provides the features of artificial liver assist devices with that of bio-artificial liver support systems.

10 Claims, 7 Drawing Sheets

INTEGRATED HYBRID BIO-ARTIFICIAL LIVER BIOREACTOR DESIGN AND METHOD THEREOF

FIELD OF THE INVENTION

The present invention relates to the field of bio-artificial liver technology. Particularly, the invention provides an integrated hybrid bio-artificial liver support system that provides the features of artificial liver assist devices with that of bio-artificial liver support systems.

BACKGROUND AND THE PRIOR ART

Liver failure accounts for a large number of deaths globally. One of the major treatment strategies for liver failure is liver transplantation, wherein a part of the donor organ is transplanted into the recipient. Although a successful form of treatment for liver failure, liver transplantation has a major limitation in the form of shortage of donors. To overcome this problem of limited donors, extracorporeal artificial liver assist devices have been developed that work on the principle of physical/chemical gradients and adsorption to remove the water soluble toxins in the blood/plasma. However, apart from detoxification, the liver is also largely involved in synthetic functions, such as, the synthesis of albumin. These synthetic functions are not replaced by the artificial liver assist devices in use clinically. Bio-artificial liver devices consist of a cell housing bioreactor that is able to replace most of the functions of the liver including metabolism and synthesis.

Many designs have been proposed for use as bio artificial liver device, including but not limited to the flat bed bioreactor and perfused bed bioreactor and the more widely accepted hollow fiber bioreactor. The hollow fiber bioreactor system allows for immune-isolation and protects the cells from shear stress, a major disadvantage with the other designs.

Typically the bioreactor system is connected externally to a plasma separator system that separates out the plasma that enters the bioreactor from blood circulated extracorporeally. Plasma passing through the bioreactor system is treated by the cells housed in it and returned to the patient. However, such systems lack efficiency and are also complicated in processing.

The existing bio artificial technology revolves around modifying the design of hollow fiber bioreactor design or modifying the cell types being used in the existing designs for bioartificial liver systems. In one of the patents filed (WO 1992007615A1), the inventors have modified the hollow fiber bioreactor system by inoculating hepatocytes into a hollow fiber in a solution that forms a highly porous gel that contracts, leaving an open channel within the hollow fiber. That is the gel matrix (made of collagen) contracts within the hollow fiber lumen to facilitate perfusion, while plasma/serum flows around the hollow fiber.

In U.S. Pat. No. 7,160,719B2, the inventors have designed a bioreactor comprising a selectively permeable baffler that separates the fluid treatment compartment from the cell compartment.

In yet another patent filed related to Bioartificial Liver (U.S. Pat. No. 5,605,835A), a bioreactor was designed to maintain animal cells in a functioning state over extended periods of time wherein a permeable membrane divides the interior into a cell chamber and a cell nutrient and waste chamber in which the cell chamber constitutes a biocompatible matrix entrapped with cells.

All these designs have tried to improve the functionality of the cells within the bioreactor system, by compartmentalizing the cells to prevent exposure to toxins. However each of these reactors needs to be connected to a separate plasma separation unit that separates out the plasma that will eventually flow through these reactor systems. This inevitably increases the overall volume of blood that is drawn out of the body resulting in stress on the body due to blood loss. Also, in all the designs mentioned above, the surface area available for the entrapped cells to grow is lesser as compared to the surface area provided by a cryogel system.

WO2016015371 relates to a bio-artificial liver system comprising plasma separation/blood transfusion cycle, a bioreactor cycle, and a cell renewing system. However, here in this system all the three parts are in communication through pipelines.

CN2638736 relates to a heterozygotic artificial liver support apparatus which includes an integrated control circuit, an input end, a plasma separation device, a plasma exchange device, a plasma absorption device, a biological response device, a plasma output device and an output end. Here also, all the components are connected through pipelines.

There exists a need for a hybrid bio artificial liver support system that integrates the components of the artificial liver and bio artificial liver assist device in a single unit including detoxifier, cell seeded bioreactor, plasma separator etc. and still capable of performing multiple hepatic functions efficiently.

Objective(s) of the Invention

An objective of the present invention is to overcome the drawback/disadvantages of the previous inventions.

Another objective of the present invention, is to provide an integrated hybrid bio-artificial liver support system that may be connected extra-corporeally to provide temporary support to a failing liver.

Another objective of the present invention, is to provide a hybrid bio-artificial liver support system where all the chambers are adapted to be positioned as an integrated and a single unit.

In another objective of the present invention, an integrated hybrid bio-artificial liver support system is provided having a plasma separation unit, detoxifier unit and bioreactor system integrated in it.

Another objective of the present invention, is to provide an integrated hybrid bio-artificial liver support system with higher surface area available for entrapping liver cells ensuring greater extent of purification.

In another objective of the present invention, an integrated hybrid bio-artificial liver support system which minimizes blood volume drawn out for extracorporeal circulation and enables maximum plasma detoxification is provided for.

Another object of the present invention, is to provide a method for detoxification of the plasma using the aforementioned integrated hybrid bio-artificial liver support system.

SUMMARY OF THE INVENTION

In an aspect of the invention, there is provided a hybrid Bio artificial liver bioreactor comprising at least three chambers wherein said chambers are adapted to be positioned as an integrated and a single unit where
  a top chamber, provided with respective inlet/outlet port, comprising a plasma separation membrane for separating a blood stream received from a patient into plasma and blood cells;

a middle chamber, provided with respective inlet/outlet port to connect with other chambers, comprising a bioreactor seeded with hepatocyte cells in the presence of semi-interpenetrating supermacroporous cryogel;

a bottom chamber, provided with respective inlet/outlet port to connect with other chambers, comprising a means for plasma collection and a means for optional reintroduction of said plasma or part thereof to said chambers where said top and middle chamber are adapted to be separated in position by the presence of a means for filtering the toxic compounds and where said middle and bottom chamber are adapted to be separated in position by the presence of a means for trapping the cellular material from leaking out of said reactor.

In another aspect of the invention, there is provided a method to detoxify plasma by the hybrid Bioartificial liver bioreactor as, comprising the steps of:

a) separating plasma from whole blood sample through said aforementioned top chamber where the separated plasma passes to said middle chamber through said means for filtering the toxic compounds while the blood cells exits from outlet of said top chamber;

b) detoxifying the plasma resulting from said top chamber of step (a) by treating with said hepatocytes cells seeded in the presence of semi-interpenetrating supermacroporous cryogel in said middle chamber where said treated plasma resulting from said middle chamber passes to said bottom chamber through said means for trapping the cellular material and passing the treated plasma to the said bottom chamber for collection.

In another aspect of the Invention, there is provided a hybrid Bioartificial liver bioreactor acting as a perfusion system for the large scale culturing of hepatocytes cells wherein said bioreactor is customized by removing said top chamber and said means for filtering the toxic compounds while connecting an additional media reservoir to said middle chamber.

DETAILED DESCRIPTION OF THE INVENTION

The present invention provides an integrated hybrid bio-artificial liver support system that may be connected extracorporeally to provide temporary support to a failing liver.

The hybrid integrated bio artificial liver support system combines the detoxification principle of the artificial liver assist devices and the biological component of the bio artificial liver devices.

The bio artificial liver support system is a multi-chamber system that can house the activated carbon, cell-seeded bioreactor as well as the plasma separator all in one unit.

The hybrid Bioartificial liver bioreactor comprises at least three grooved chambers wherein said chambers are adapted to be positioned as an integrated and a single unit wherein a top chamber, provided with respective inlet/outlet port, comprising a plasma separation membrane for separating a blood stream received from a patient into plasma and blood cells;

a middle chamber, provided with respective inlet/outlet port to connect with other chambers, comprising a bioreactor seeded with hepatocyte cells in the presence of semi-interpenetrating supermacroporous cryogel;

a bottom chamber, provided with respective inlet/outlet port to connect with other chambers, comprising a means for plasma collection and a means for optional reintroduction of said plasma or part thereof to said chambers where said top and middle chamber are adapted to be separated in position by the presence of a means for filtering the toxic compounds and where said middle and bottom chamber are adapted to be separated in position by the presence of a means for trapping the cellular material from leaking out of said reactor.

Figure 1A:
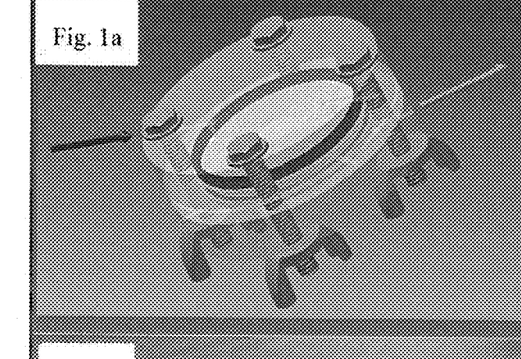
FIGS. 1A-1C: illustrates A) Tilted view of the three-chambered bio-artificial liver device; B) Digital image of the Bio-artificial liver device; C) Blown-up version of the three-chambered bioreactor system showing the individual components of the device. The red arrow indicates flow of blood into the device, whereas the shaded arrow indicates the flow of plasma out of the unit.
Figure 1B:
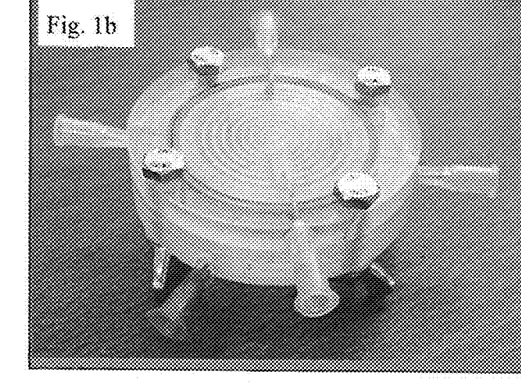
Figure 1C:
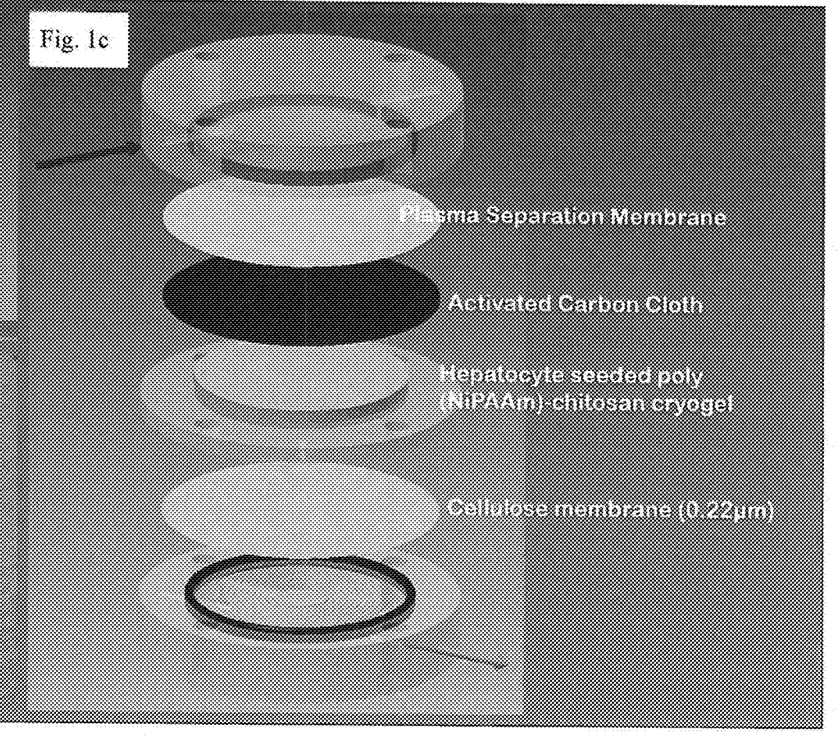

In an embodiment, the bioartificial liver support system is a three-chambered bioreactor system with the integration of a plasma separation unit and a detoxifier unit with a bioreactor system in a single unit. In this embodiment, the design constitutes of a semi-interpenetrating network supermacroporous cryogel of Poly(N-isopropylacrylamide)-chitosan seeded with hepatocytes (liver cells) housed in a three-chambered reactor system (as illustrated in FIG. 1). In another embodiment, the cryogel is a polymer with optional coating of porcine decellularised liver matrix, where said polymer is selected from poly(n-isopropylacrylamide)-chitosan, alginate, galactosylated chitosan, polyethylene glycol (PEG) or alike material.

Figure 2:
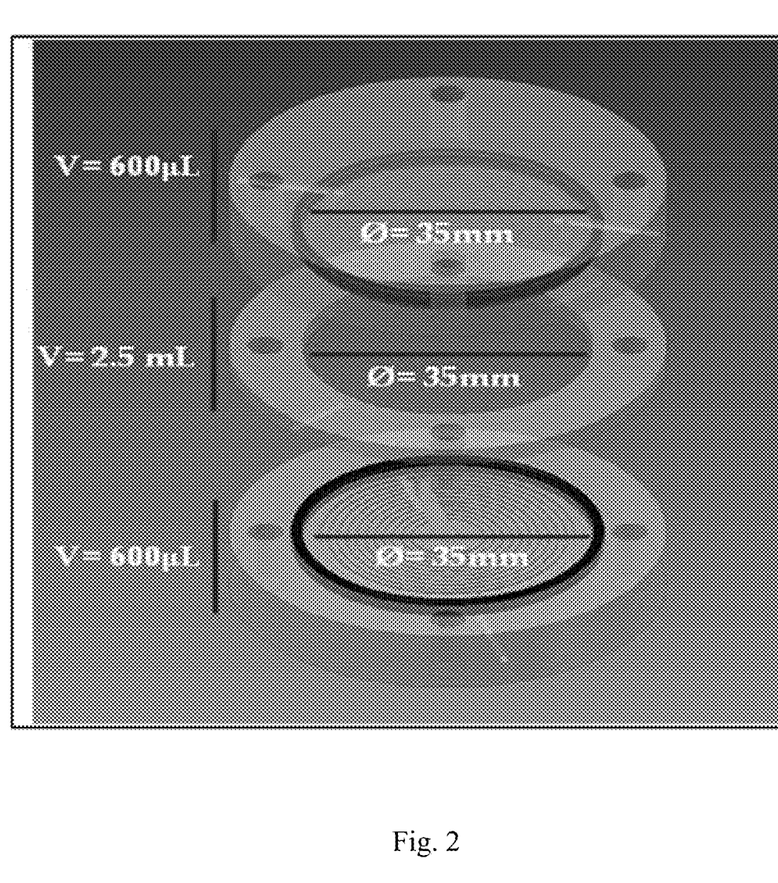
FIG. 2: illustrates Dimensions of an embodiment of the Bioreactor System of the present Invention
Figure 3A:
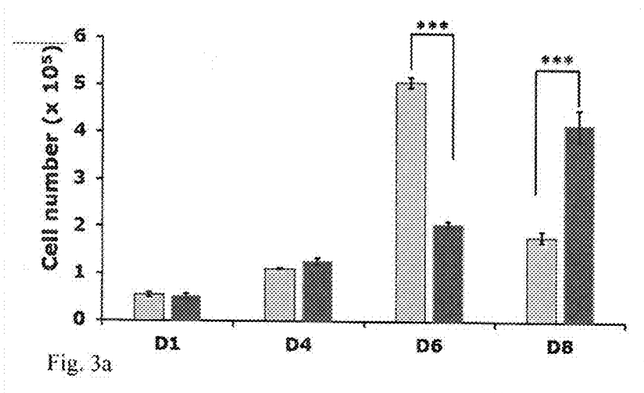
FIGS. 3A-3D: illustrates Graphs representing cell viability (A), and hepatocyte functionality in terms of albumin synthesized (B), CytochromeP450 activity (C) and Urea synthesized (D) over a period of a week; where n=3, *** $p<0.005$ (paired t-test used for statistical analysis)
Figure 3B:
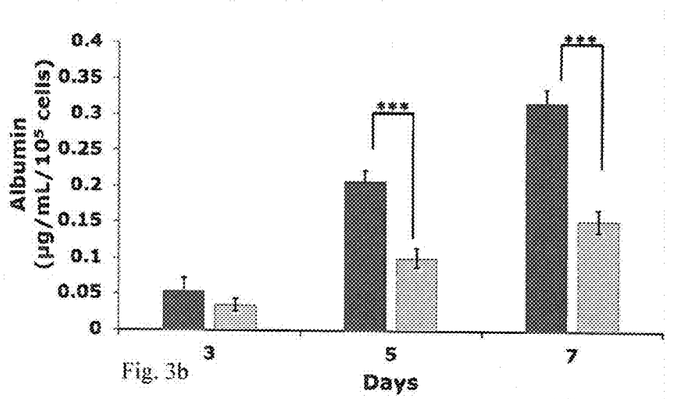
Figure 3C:
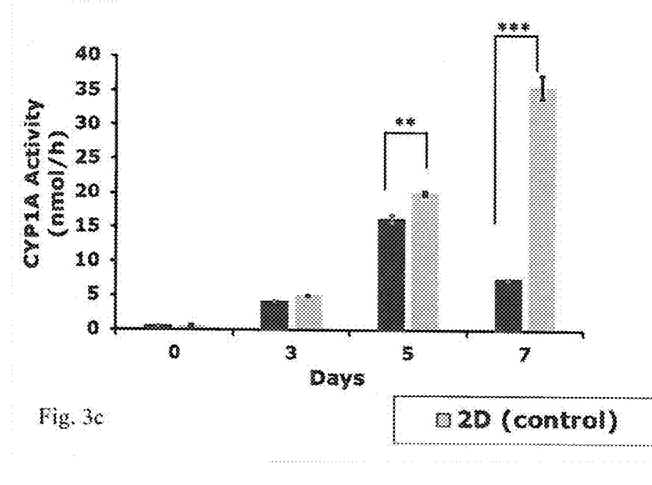
Figure 3D:
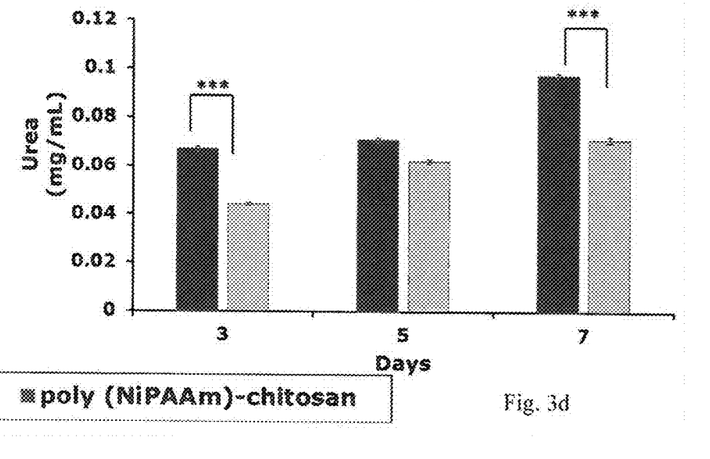

In another embodiment, the top chamber and middle chamber have a depth of approximately 1 mm, resulting in a volume that is approximately 600 μL (as illustrated in FIG. 2). All the chambers are grooved so as to allow for maximum exposure of the blood to the membrane systems, resulting in more efficient plasma separation in the top chamber and plasma collection in the bottom chamber.

In another embodiment, the middle chamber has a depth of approximately 2-3 mm, so as to allow the cryogel sheet of similar thickness to fit in. The overall volume of the entire bioreactor design is approximately 3.5 to 4 mL.

In another embodiment, the top-most chamber contains a plasma separation membrane that is used to filter out the blood cells and allow passage of plasma to the middle chamber.

In another embodiment, the middle chamber is separated from the top chamber by a means for filtering the toxic compounds of blood that filters out the toxic components of blood preventing their passage to the middle chamber.

In another embodiment, such a means for filtering the toxic compounds comprises a thin sheet of activated charcoal, cryogel sheet of activated carbon with/without zeolite or likewise agent.

In another embodiment, such a means for trapping the cellular material comprises a thin sheet of cellulose or alike material.

The middle chamber is the one that houses the supermacroporous cryogel seeded with hepatocytes.

In another embodiment, the middle and bottom chamber is partitioned by the presence of a means for trapping the cellular material from leaking out of the reactor. Such means for trapping the cellular material comprises a 0.22 μm cellulose membrane that traps any cellular material from leaking out of the reactor.

The depth of each chamber is selected so as to obtain an optimum volume for each chamber and minimize the total volume of the bioreactor.

In another embodiment, the bioreactor comprises peristaltic pumps for pumping the treated plasma from the bottom chamber to the patient and for the extracorporeal circulation of the blood from the patient.

In another aspect of the Invention, the integrated hybrid bio-artificial liver support system causes the purification of blood. In an embodiment of such aspect of the Invention, the blood enters from the inlet of the top chamber and exits from the outlet of the top chamber.

In another aspect of the Invention, the integrated hybrid bio-artificial liver support system causes separation of plasma in the top chamber, passes through the middle chamber and exits from the outlet of the bottom chamber (after being treated by the cryogel seeded with hepatocytes).

In another aspect of the Invention, the integrated hybrid bio-artificial liver support system facilitates the circulation of nutrients like glucose, saline and other forms of nutrients to the cells seeded in the cryogel matrix in the middle chamber through the inlet/outlet in this chamber.

In another embodiment of the invention, a part of the plasma leaving the bottom chamber may be looped to enter via the inlet of the middle chamber so as to allow more efficient treatment of the plasma by the cell seeded cryogel matrix.

In another aspect of the Invention, the bioreactor designed is used as a perfusion-based system for the large scale culturing of hepatocytes at the laboratory scale, wherein the plasma separation membranes and activated charcoal sheet are removed and the bioreactor containing cell seeded cryogel matrix is connected to a media reservoir. In an embodiment of such aspect of the Invention, the media is perfused through the bioreactor system at a flow rate 0.2 mL/min.

In another aspect of the invention, there is provided a method to detoxify the plasma comprising steps of:
 a) separating plasma from whole blood of the mammal through said top chamber where the separated plasma passes to said middle chamber through said means for filtering the toxic compounds;
 b) treating the plasma resulting from said top chamber of step (a) with said hepatocytes cells seeded in the presence of semi-interpenetrating supermacroporous cryogel in said middle chamber where said treated plasma resulting from said middle chamber passes to said bottom chamber through said means for trapping the cellular material and passing the detoxified plasma to the said bottom chamber for collection.

The depth of each chamber is selected so as to obtain an optimum volume for each chamber and minimize the total volume of the bioreactor.

The invention is further described with the help of non-limiting examples:

Example 1

Figure 4A:
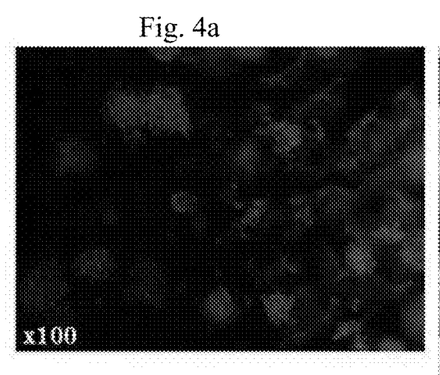
FIGS. 4A-4B: illustrates A) Fluorescence Microscopic Image showing nuclear staining (using DAPI) of the hepatocytes seeded in cryogel matrix B) Scanning Electron Microscopic Image showing the hepatocytes seeded in cryogel matrix
Figure 4B:
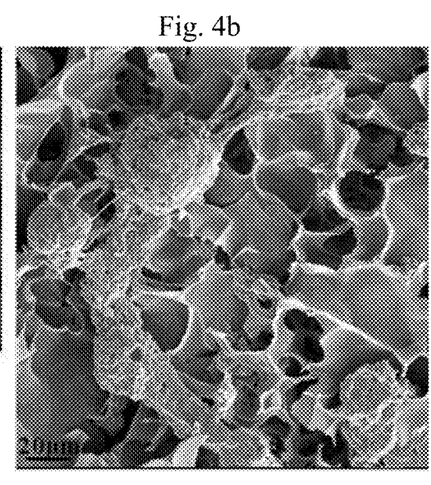
Figure 5A:
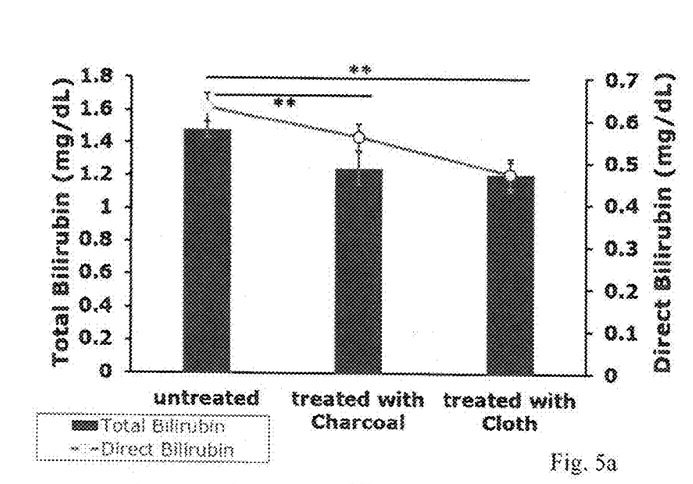
FIGS. 5A-5D: illustrates A) Total and direct bilirubin concentration; B) urea and ammonia concentration; C) albumin concentration; D) SGOT or AST concentration; before and after treatment with activated charcoal as well as activated carbon cloth; n=3,  $p<0.05$, * $p<0.005$ (paired t-test used for statistical analysis)
Figure 5B:
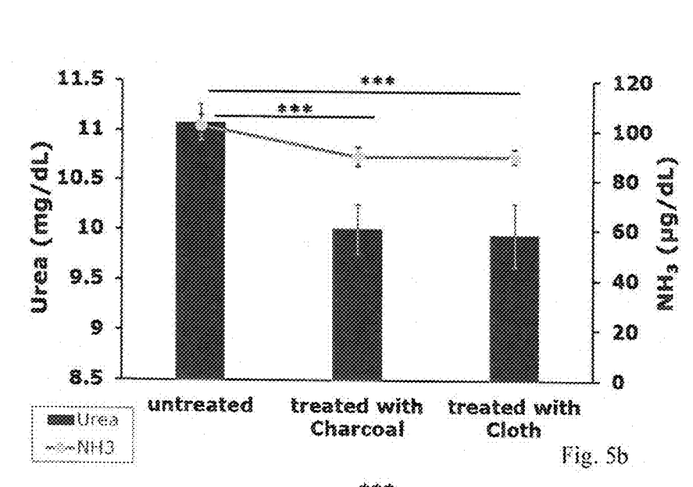
Figure 5C:
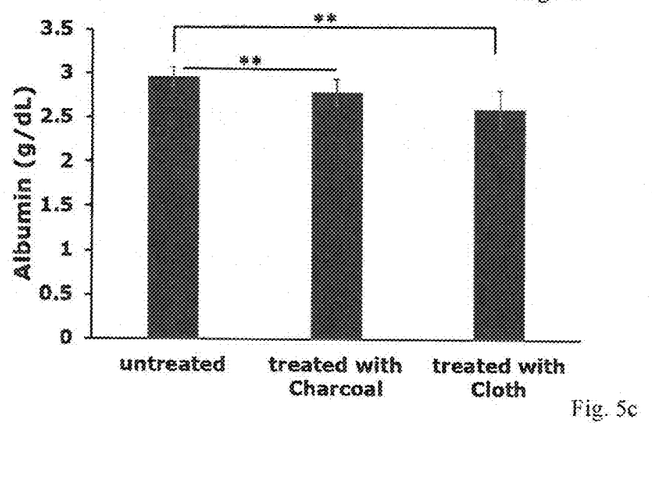
Figure 5D:
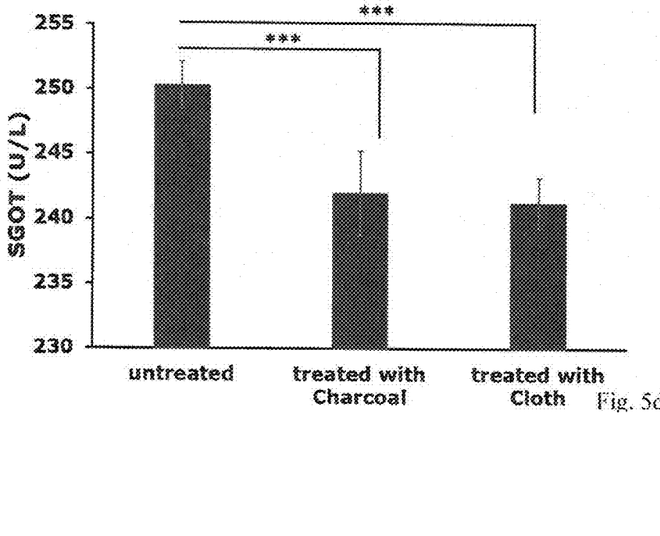
Figure 6A:
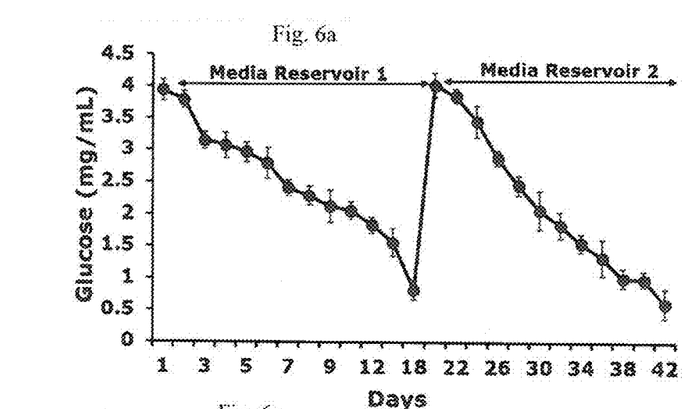
FIGS. 6A-6D: illustrates A) Glucose consumption by HepG2 cells seeded in poly(NiPAAm)-chitosan cryogel bioreactor over a period of 42 days; B) ammonia accumulation in HepG2 seeded poly(NiPAAm)-chitosan cryogel bioreactor; C) albumin synthesis in poly(NiPAAm)-chitosan cryogel bioreactor over a period of 42 days; D) scanning electron microscopic image of HepG2 cells seeded in the poly(NiPAAm)-chitosan cryogel at the end of 42 days of perfusion culture.
Figure 6B:
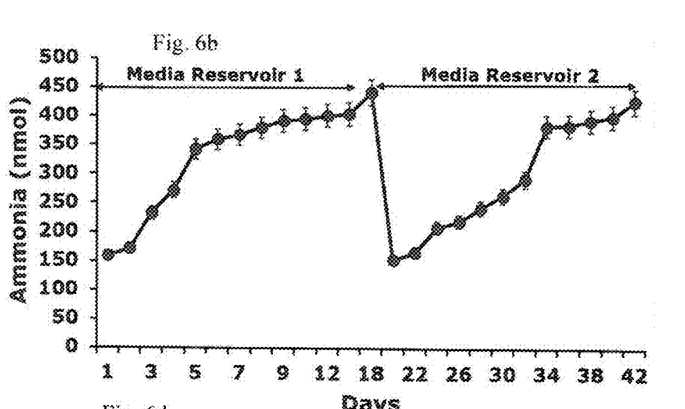
Figure 6C:
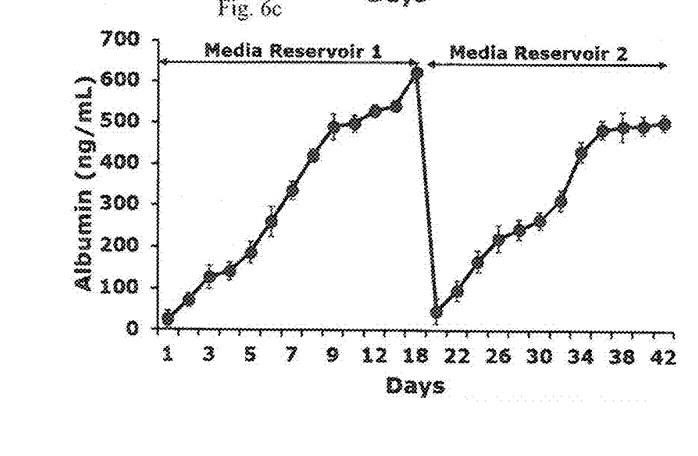
Figure 6D:
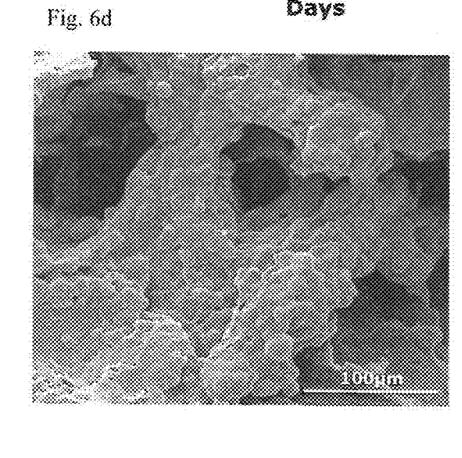
Figure 7A:
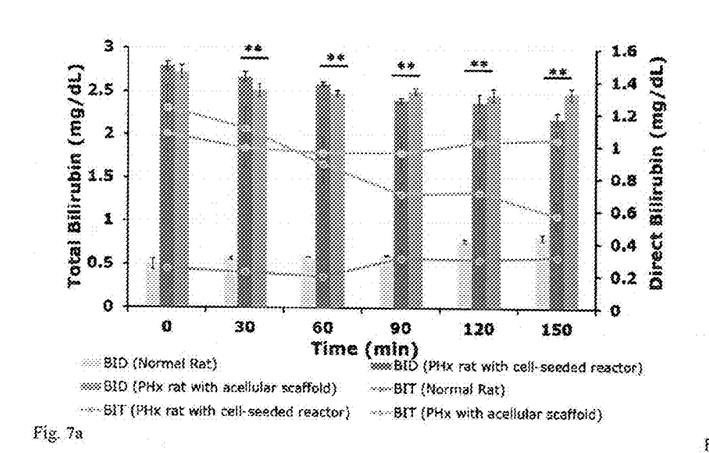
FIGS. 7A-7D: illustrates Levels of total and direct bilirubin (A), urea and ammonia (B), SGOT (C), and microalbumin (D) in samples of rat plasma collected at 30 min intervals during extracorporeal connection of the developed Bio-artificial liver support device (with and without cell seeded scaffold) to a rat model of acute liver failure; PHx-Partial Hepatectomy; n=4, * $p<0.5$,  $p<0.05$, * $p<0.005$, # ns (paired t-test was used for statistical significance)
Figure 7B:
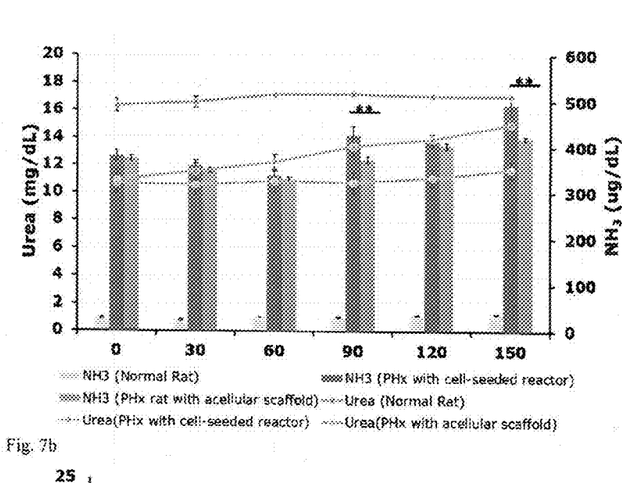
Figure 7C:
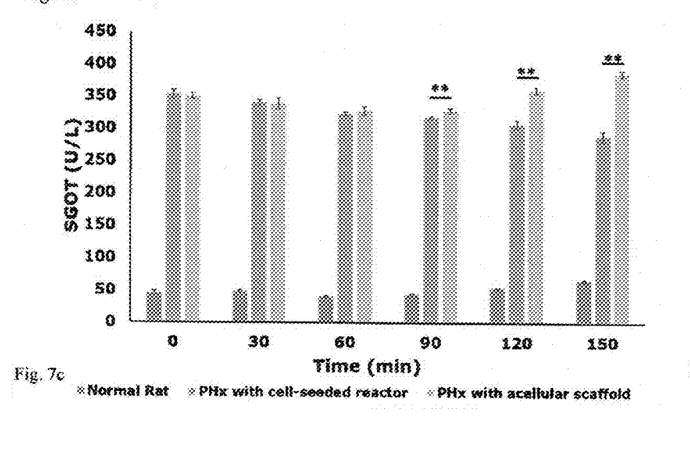
Figure 7D:
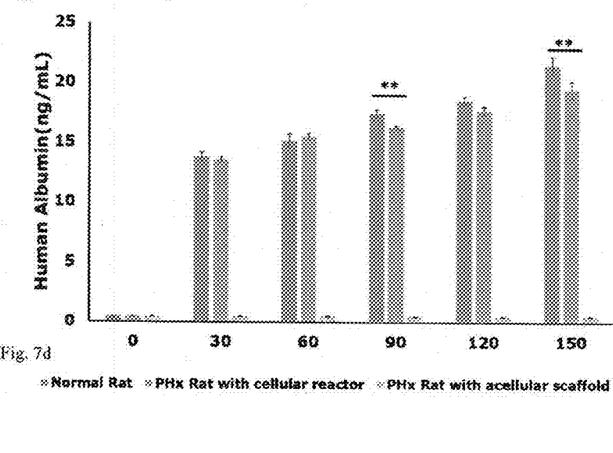

Cell-Material Interactions:
Growing Hepatocytes on Poly(N-Isopropylacrylamide)-Chitosan Semi-Interpenetrating Network Cryogels:
Preliminary in vitro studies involved seeding poly (N-isopropylacrylamide)-chitosan cryogels with hepatocytes (HepG2 cell line) and studying the cell viability as well as functionality of the cells on the scaffold. HepG2 cells were seeded on sterilized scaffolds and cell viability was checked using MTT assay, whereas cell functionality was measured in terms of albumin and urea synthesis (as illustrated in FIG. 3). Results from the MTT assay suggested the ability of the cells to proliferate on the cryogel scaffolds, whereas results from albumin and urea assay showed the ability of the cells to maintain their functionality on the cryogel matrix. In addition, the cells were fixed on the cryogel matrices using 2.5% glutaraldehyde and observed using Scanning Electron Microscopy (SEM) to check for their adherence and morphology on the scaffold. Cell viability was microscopically confirmed using the nuclear stain DAPI (as illustrated in FIG. 4).

Example 2

Another study was performed to find the effect of activated charcoal sheet on plasma treatment. The previous studies with the plasma obtained from patients with acute-liver failure showed toxic effects on the cells seeded in the cryogel matrix, resulting in loss of viability and functionality. Thus, it was required to remove circulating toxins in the plasma before it passes through the cell-loaded cryogel matrix in the middle chamber.

Studies using plasma from a rat model of acute-liver failure showed the ability of the activated charcoal cryogel as well as the cloth to remove a majority of the toxins found in the plasma such as bilirubin, ammonia and urea (as illustrated in FIG. 5).

Example 3

Another experiment was performed for the perfusion based reactor initial studies where three-chambered bioartificial liver unit was used as a perfusion-based bioreactor system to culture liver cells on the cryogel scaffold. For this, the sterile cryogel to be seeded is placed in the middle chamber, supported on a 0.22 µm cellulose membrane. Cell suspension is passed through the top chamber and allowed to reach the middle chamber. At first all outlets are closed so as to allow the cells to adhere to the cryogel matrix. After 4-5 h, the outlet in the bottom chamber is opened and fresh media perfused through the matrix at a rate of 0.2 mL/min Initial run through is collected to check for any cell loss. Samples of spent media are collected at one day intervals and analyzed for albumin synthesis, glucose consumption and ammonia accumulation in the reactor system. The results showed an increase in the albumin levels over a period of time with a decrease in glucose levels in the reactor, suggesting that the cells were functioning effectively in the perfusion bioreactor system (as illustrated in FIG. 6).

Example 4

Study was Performed for Extracorporeal Connection of Bioreactor to Animal Model

To further study the efficacy of the developed Bio-artificial liver support, the bioreactor setup is connected to an animal model for acute liver failure (The animal study was carried out under Institute animal ethics committee approval # IITK/IAEC/2014/1022). Partial hepatectomy (70%) followed by ischemic reperfusion for 30 minutes (in which most of the right lobe of the liver is removed) is performed on male Wistar rats weighing between 200-250 g, and after an hour (the time required for the effect of the hepatectomy to set in), the animal is connected to the bioreactor through the carotid artery and jugular vein. Through literature survey, it is known that this kind of an animal model can survive on a bioartificial support for approximately 3-4 h. In our case, it was observed that on an average, the animal was able to survive for a time period of 3 h on the reactor.

Liver function parameters (total and direct bilirubin, serum glutamate oxaloacetic transaminase (SGOT), ammonia, urea and micro-albumin) were studied while the model animal was connected on the bioreactor. It was observed that the total bilirubin levels in the model animal reduced significantly over a period of 3 hours as was the case with SGOT, while the levels of urea and micro-albumin (human albumin synthesized by HepG2 cells seeded in the bioreactor) increased significantly. However, the levels of ammonia remained relatively unchanged during the first hour and later increased. This trend in ammonia level could be explained by the inability of HepG2 cells to detoxify ammonia (as illustrated in FIG. 7).

We claim:

1. A hybrid Bioartificial liver bioreactor comprising:
at least three chambers adapted to be positioned as ax integrated and a single unit including:
a top chamber, provided with a first inlet/outlet port, comprising a plasma separation membrane configured to separate a blood stream received from a patient into plasma and blood cells;
a middle chamber, provided with a second inlet/outlet port to connect with the top or a bottom chamber, said middle chamber seeded with hepatocyte cells in a semi-interpenetrating supermacroporous cryogel;
the bottom chamber provided with a third inlet/outlet port to connect with the top or middle chambers, the bottom chamber configured for plasma collection and reintroduction of said plasma or part thereof to one of said top or middle chambers;
where said top and middle chambers are configured to be separated in position by a means for filtering, toxic compounds, and
where said middle and bottom chambers are separated by a means for trapping cellular material from leaking out of said bioreactor.

2. The hybrid Bioartificial liver bioreactor as claimed in claim 1, wherein said at least three chambers are configured to be in communication with each other.

3. The hybrid Bioartificial liver bioreactor as claimed in claim 1, wherein said at least three chambers are grooved.

4. The hybrid Bioartificial liver bioreactor as claimed in claim 1, wherein said means for filtering the toxic compounds comprises a thin sheet of activated charcoal or a cryogel sheet of activated carbon with/without zeolite.

5. The hybrid Bioartificial liver bioreactor as claimed in claim 1, wherein said means for trapping the cellular material comprises a thin sheet of cellulose.

6. The hybrid Bioartificial liver bioreactor as claimed in claim 1, wherein said semi-interpenetrating supermacroporous cryogel is a polymer with a coating of porcine decellularised liver matrix, where said polymer is selected from poly(n-isopropylacrylamide)-chitosan, alginate, galactosylated chitosan, or polyethylene glycol (PEG).

7. The hybrid Bioartificial liver bioreactor as claimed in claim 1, wherein a volume of said hybrid Bioartificial liver bioreactor is approximately 3.5 ml to 4 ml.

8. The hybrid Bioartificial liver bioreactor as claimed in claim 1, wherein nutrients are circulated to said middle chamber comprising hepatocyte cells seeded in said semi-interpenetrating supermacroporous cryogel.

9. A method to detoxify plasma by the hybrid Bioartificial liver bioreactor of claim 1, comprising the steps of:
a) separating plasma from whole blood sample through said top chamber where the separated plasma passes to said middle chamber through said means for filtering the toxic compounds while the blood cells exits from outlet of said top chamber; and
b) detoxifying the plasma resulting from said top chamber of step (a) by treating with said hepatocytes cells seeded in the presence of semi-interpenetrating supermacroporous cryogel in said middle chamber where said treated plasma resulting from said middle chamber passes to said bottom chamber through said means for trapping the cellular material and passing the treated plasma to the said bottom chamber for collection.

10. A hybrid Bioartificial liver bioreactor comprising:
at least three chambers adapted to be positioned as an integrated and a single unit, the at least three chambers including a top chamber having a top chamber inlet/outlet port, comprising means for separating a blood stream received from a patient into plasma and blood cells,
a middle chamber, provided with a middle chamber inlet/outlet port to connect with the top or a bottom chamber, said middle chamber seeded with hepatocyte cells in a semi-interpenetrating supermacroporous cryogel, the bottom chamber provided with a bottom chamber inlet/outlet port to connect with the top or middle chambers, the bottom chamber configured for collecting plasma and reintroducing plasma or part thereof to one of said top or middle chambers; and
a filter configured to filter toxic compounds, said filter separating the top and middle chambers; and a membrane separating the middle and bottom chambers configured to trap cellular material from leaking out of said middle chamber.

\* \* \* \* \*

UNITED STATES PATENT AND TRADEMARK OFFICE
CERTIFICATE OF CORRECTION

PATENT NO. : 10,245,368 B2  
APPLICATION NO. : 15/224055  
DATED : April 2, 2019  
INVENTOR(S) : Kumar et al.

Page 1 of 1

It is certified that error appears in the above-identified patent and that said Letters Patent is hereby corrected as shown below:

In the Claims

Column 7, Line 53, please replace "ax" with --an--.

Signed and Sealed this  
Twenty-fifth Day of June, 2019

Andrei Iancu  
*Director of the United States Patent and Trademark Office*